United States Patent [19]

Yankee

[11] 4,118,579
[45] Oct. 3, 1978

[54] 5-OXA-11-DEOXY-CIS-13-PGF$_1$ COMPOUNDS

[75] Inventor: Ernest W. Yankee, Portage, Mich.

[73] Assignee: The Upjohn Company, Kalamazoo, Mich.

[21] Appl. No.: 774,080

[22] Filed: Mar. 3, 1977

Related U.S. Application Data

[62] Division of Ser. No. 595,869, Jul. 14, 1975, Pat. No. 4,026,909.

[51] Int. Cl.$^2$ ............................................ C07C 177/00
[52] U.S. Cl. ...................................... 560/121; 562/503
[58] Field of Search .......................... 260/468, 514, 69; 560/121

[56] References Cited

U.S. PATENT DOCUMENTS 3,932,479  1/1976  Bernady ............................... 260/448

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is of the cis configuration. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

21 Claims, No Drawings

5-OXA-11-DEOXY-CIS-13-PGF$_1$ COMPOUNDS

The present application is a divisional application of Ser. No. 595,869, filed July 14, 1975, now issued as U.S. Pat. No. 4,026,909 on May 31, 1977.

The present invention relates to prostaglandin analogs for which the essential material constituting a disclosure therefor is incorporated by reference here from U.S. Pat. No. 4,026,909, issued May 31, 1977.

What is claimed is:

1. A compound of the formula

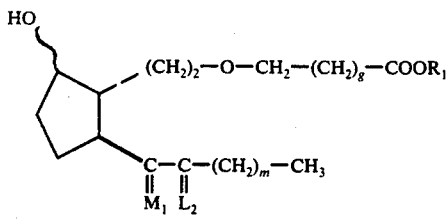

wherein $g$ is 2, 3, or 4;
wherein Y is cis—CH=CH—;
wherein M$_1$ is

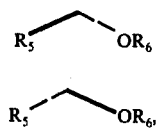

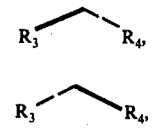

wherein R$_5$ and R$_6$ are hydrogen or methyl, with the proviso that one of R$_5$ and R$_6$ is methyl only when the other is hydrogen;
wherein L$_2$ is

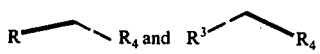

or a mixture of wherein R$_3$ and R$_4$ are hydrogen, methyl, or fluoro, being the same or different, with the proviso that at least one of R$_3$ and R$_4$ is methyl or fluoro and that one of R$_3$ and R$_4$ is fluoro only when the other is hydrogen or fluoro;

wherein $m$ is 1 to 5, inclusive; and
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein $g$ is 4.

3. A compound according to claim 2, wherein $m$ is 3.

4. A compound according to claim 3, wherein at least one of R$_3$ and R$_4$ is fluoro.

5. A compound according to claim 4, wherein R$_3$ and R$_4$ are both fluoro.

6. A compound according to claim 5, wherein R$_5$ and R$_6$ are hydrogen.

7. 15-epi-2a,2b-Dihomo-16,16-difluoro-5-oxa-11-deoxy-cis-13-PGF$_1\alpha$, methyl ester, a compound according to claim 6.

8. A compound according to claim 3, wherein at least one of R$_3$ and R$_4$ is methyl.

9. A compound according to claim 8, wherein R$_3$ and R$_4$ are both methyl.

10. A compound according to claim 9, wherein R$_5$ and R$_6$ are both hydrogen.

11. 15-epi-2a,2b-Dihomo-16,16-dimethyl-5-oxa-11-deoxy-cis-13-PGF$_1\alpha$, methyl ester, a compound according to claim 10.

12. A compound according to claim 11, wherein $g$ is 2.

13. A compound according to claim 12, wherein $m$ is 3.

14. A compound according to claim 13, wherein at least one of R$_3$ and R$_4$ is fluoro.

15. A compound according to claim 14, wherein both R$_3$ and R$_4$ are fluoro.

16. A compound according to claim 15, wherein R$_5$ and R$_6$ are hydrogen.

17. 15-epi-16,16-Difluoro-5-oxa-11-deoxy-cis-13-PGF$_1\alpha$, methyl ester, a compound according to claim 16.

18. A compound according to claim 13, wherein at least one of R$_3$ and R$_4$ is methyl.

19. A compound according to claim 18, wherein R$_3$ and R$_4$ are both methyl.

20. A compound according to claim 19, wherein R$_5$ and R$_6$ are hydrogen.

21. 15-epi-16,16-Dimethyl-5-oxa-11-deoxy-cis-13-PGF$_1\alpha$, methyl ester, a compound according to claim 20.

* * * * *

UNITED STATES PATENT OFFICE
CERTIFICATE OF CORRECTION

Patent No. 4,118,579      Dated October 3, 1978

Inventor(s) Ernest W. Yankee

It is certified that error appears in the above-identified patent and that said Letters Patent are hereby corrected as shown below:

In the title: "PGF,₁ COMPOUNDS" should read -- PGF₁ COMPOUNDS --.

Column 1, lines 19-21, that portion of the formula reading

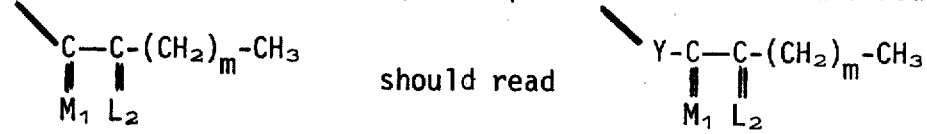

should read

Column 1, lines 48-49,

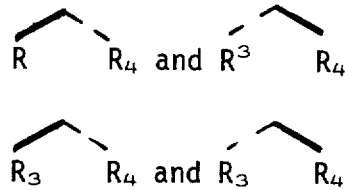

should read

Column 2, line 31, "according to claim 11" should read -- according to claim 1 --.

Signed and Sealed this

Twentieth Day of February 1979

[SEAL]

Attest:

RUTH C. MASON
*Attesting Officer*

DONALD W. BANNER
*Commissioner of Patents and Trademarks*